United States Patent
Weisenburgh, II et al.

(10) Patent No.: US 8,915,842 B2
(45) Date of Patent: Dec. 23, 2014

(54) METHODS AND DEVICES FOR MAINTAINING VISIBILITY AND PROVIDING IRRIGATION AND/OR SUCTION DURING SURGICAL PROCEDURES

(75) Inventors: William B. Weisenburgh, II, Maineville, OH (US); Carl J. Shurtleff, Mason, OH (US); Darrel M. Powell, Cincinnati, OH (US); Christopher J. Hess, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1731 days.

(21) Appl. No.: 12/172,349

(22) Filed: Jul. 14, 2008

(65) Prior Publication Data

US 2010/0010310 A1     Jan. 14, 2010

(51) Int. Cl.
| | |
|---|---|
| *A61B 1/00* | (2006.01) |
| *A61B 1/015* | (2006.01) |
| *A61B 1/12* | (2006.01) |
| *A61B 1/313* | (2006.01) |

(52) U.S. Cl.
CPC ............ *A61B 1/015* (2013.01); *A61B 1/00135* (2013.01); *A61B 1/00091* (2013.01); *A61B 1/126* (2013.01); *A61B 1/3132* (2013.01)
USPC ............ 600/156; 600/157; 600/158; 600/121

(58) Field of Classification Search
USPC ......... 600/104, 106, 107, 121–125, 155–159; 604/95.01–102.03
See application file for complete search history.

(56) References Cited

U.S. PATENT DOCUMENTS

| | | | |
|---|---|---|---|
| 3,850,162 A | 11/1974 | Iglesias | |
| 4,207,874 A | 6/1980 | Choy | |
| 4,245,624 A * | 1/1981 | Komiya | ..................... 600/106 |
| 4,281,646 A | 8/1981 | Kinoshita et al. | |

(Continued)

FOREIGN PATENT DOCUMENTS

| | | |
|---|---|---|
| CA | 2661238 A1 | 10/2009 |
| DE | 19619065 A1 | 11/1997 |

(Continued)

OTHER PUBLICATIONS

European Search Report relating to EP Application No. 09251789.5-1269 dated Oct. 1, 2009.

(Continued)

*Primary Examiner* — Matthew J Kasztejna
*Assistant Examiner* — Ryan Henderson

(57) ABSTRACT

Methods and devices are provided for providing irrigation and/or suction to a surgical site and maintaining clear visibility through a lens of a scoping device during a surgical procedure. In general, the methods and devices can allow for a surgical instrument to maintain visibility during a surgical procedure using a fluid conduit coupled to the surgical instrument. A surgical device can include a sheath having at least one lumen extending therethrough configured to allow a surgical viewing instrument to be disposed therein. The sheath can also have a passageway extending therethrough configured to allow fluid to flow therethrough. The fluid conduit can be configured to be movable between positions that can allow alternative directions of fluid toward and/or away from a viewing element on the surgical instrument and fluid away from the viewing element and toward a surgical field in a body cavity.

21 Claims, 12 Drawing Sheets

(56) References Cited

U.S. PATENT DOCUMENTS

| | | |
|---|---|---|
| 4,408,598 A | 10/1983 | Ueda et al. |
| 4,567,880 A | 2/1986 | Goodman |
| 4,576,146 A | 3/1986 | Kawazoe et al. |
| 4,617,013 A | 10/1986 | Betz |
| 4,741,326 A | 5/1988 | Sidall et al. |
| 4,760,838 A | 8/1988 | Fukuda et al. |
| 4,770,163 A | 9/1988 | Ono et al. |
| 4,852,551 A | 8/1989 | Opie et al. |
| 4,874,364 A | 10/1989 | Morris et al. |
| 4,877,016 A | 10/1989 | Kantor et al. |
| 4,878,894 A | 11/1989 | Sutter et al. |
| 4,919,113 A | 4/1990 | Sakamoto et al. |
| 4,991,565 A | 2/1991 | Takahashi et al. |
| 5,019,054 A | 5/1991 | Clement et al. |
| 5,112,308 A | 5/1992 | Olsen et al. |
| 5,167,220 A | 12/1992 | Brown |
| 5,188,591 A | 2/1993 | Dorsey, III |
| 5,207,213 A | 5/1993 | Auhll et al. |
| 5,224,929 A | 7/1993 | Remiszewski |
| 5,225,001 A | 7/1993 | Manni et al. |
| 5,241,990 A | 9/1993 | Cook |
| 5,247,966 A | 9/1993 | Stevens et al. |
| 5,279,549 A | 1/1994 | Ranford |
| 5,312,351 A | 5/1994 | Gerrone |
| 5,312,400 A | 5/1994 | Bales et al. |
| 5,313,934 A | 5/1994 | Wiita et al. |
| 5,320,608 A | 6/1994 | Gerrone |
| 5,339,800 A | 8/1994 | Wiita et al. |
| 5,347,992 A | 9/1994 | Pearlman et al. |
| 5,364,341 A | 11/1994 | Cook |
| 5,386,817 A | 2/1995 | Jones |
| 5,388,612 A | 2/1995 | Cerola et al. |
| 5,391,145 A | 2/1995 | Dorsey, III |
| 5,392,766 A | 2/1995 | Masterson et al. |
| 5,400,767 A | 3/1995 | Murdoch et al. |
| 5,449,145 A | 9/1995 | Wortrich |
| 5,458,640 A | 10/1995 | Gerrone |
| 5,460,168 A * | 10/1995 | Masubuchi et al. ............ 600/123 |
| 5,464,008 A | 11/1995 | Kim |
| 5,468,240 A | 11/1995 | Gentelia et al. |
| 5,484,402 A | 1/1996 | Saravia et al. |
| 5,496,280 A | 3/1996 | Vandenbroek et al. |
| 5,514,084 A | 5/1996 | Fisher |
| 5,514,089 A | 5/1996 | Walbrink et al. |
| 5,518,501 A | 5/1996 | Oneda et al. |
| 5,536,236 A | 7/1996 | Yabe et al. |
| 5,575,756 A | 11/1996 | Karasawa et al. |
| 5,603,702 A | 2/1997 | Smith et al. |
| 5,630,795 A | 5/1997 | Kuramoto et al. |
| 5,637,075 A | 6/1997 | Kikawada et al. |
| 5,643,227 A | 7/1997 | Stevens |
| 5,643,301 A | 7/1997 | Mollenauer |
| 5,662,614 A | 9/1997 | Edoga |
| 5,697,888 A | 12/1997 | Kobayashi et al. |
| 5,957,888 A | 9/1999 | Hinchliffe |
| 5,989,183 A | 11/1999 | Reisdorf et al. |
| 5,989,224 A | 11/1999 | Exline et al. |
| 6,004,326 A | 12/1999 | Castro et al. |
| 6,110,103 A | 8/2000 | Donofrio |
| 6,126,592 A | 10/2000 | Proch et al. |
| 6,176,825 B1 | 1/2001 | Chin et al. |
| 6,217,510 B1 * | 4/2001 | Ozawa et al. ................. 600/129 |
| 6,258,065 B1 | 7/2001 | Dennis et al. |
| 6,258,083 B1 * | 7/2001 | Daniel et al. .................... 606/15 |
| 6,282,442 B1 | 8/2001 | DeStefano et al. |
| 6,354,992 B1 | 3/2002 | Kato |
| 6,364,853 B1 | 4/2002 | French et al. |
| 6,383,132 B1 | 5/2002 | Wimmer et al. |
| 6,406,425 B1 | 6/2002 | Chin et al. |
| 6,409,657 B1 | 6/2002 | Kawano et al. |
| 6,436,067 B1 | 8/2002 | Deng et al. |
| 6,447,446 B1 | 9/2002 | Smith et al. |
| 6,595,915 B2 | 7/2003 | Akiba et al. |
| 6,652,488 B1 | 11/2003 | Cover et al. |
| 6,685,665 B2 | 2/2004 | Booth et al. |
| 6,695,772 B1 | 2/2004 | Bon et al. |
| 6,702,787 B2 | 3/2004 | Racenet et al. |
| 6,712,757 B2 | 3/2004 | Becker et al. |
| 6,786,865 B2 | 9/2004 | Dhindsa |
| 6,849,042 B2 | 2/2005 | Christopher |
| 6,857,436 B2 | 2/2005 | Labib et al. |
| 6,860,869 B2 | 3/2005 | Dennis |
| 6,881,188 B2 | 4/2005 | Furuya et al. |
| 6,889,400 B2 | 5/2005 | Kawazoe et al. |
| 6,921,380 B1 | 7/2005 | Epstein et al. |
| 6,984,204 B2 | 1/2006 | Akiba et al. |
| 7,056,303 B2 | 6/2006 | Dennis et al. |
| 7,083,626 B2 | 8/2006 | Hart et al. |
| 7,112,185 B2 | 9/2006 | Hart et al. |
| 7,169,130 B2 | 1/2007 | Exline et al. |
| 7,244,244 B2 | 7/2007 | Racenet et al. |
| 7,311,660 B2 | 12/2007 | Gomez |
| 7,318,814 B2 | 1/2008 | Levine et al. |
| 7,344,519 B2 | 3/2008 | Wing et al. |
| 7,473,243 B2 | 1/2009 | Dennis et al. |
| 7,591,802 B2 | 9/2009 | Johnson et al. |
| 2002/0022762 A1 | 2/2002 | Beane et al. |
| 2002/0107484 A1 | 8/2002 | Dennis et al. |
| 2002/0173699 A1 | 11/2002 | Becker et al. |
| 2003/0060770 A1 | 3/2003 | Wing et al. |
| 2004/0059363 A1 | 3/2004 | Alvarez et al. |
| 2004/0171990 A1 | 9/2004 | Dennis et al. |
| 2004/0204679 A1 | 10/2004 | Visconti et al. |
| 2004/0260244 A1 | 12/2004 | Piechowicz et al. |
| 2005/0011952 A1 | 1/2005 | Krichever |
| 2005/0043683 A1 | 2/2005 | Ravo |
| 2005/0043690 A1 | 2/2005 | Todd |
| 2005/0065405 A1 | 3/2005 | Hasegawa |
| 2005/0070850 A1 | 3/2005 | Albrecht |
| 2005/0070946 A1 | 3/2005 | Franer et al. |
| 2005/0070947 A1 | 3/2005 | Franer et al. |
| 2005/0077688 A1 | 4/2005 | Voegele et al. |
| 2005/0077689 A1 | 4/2005 | Hueil |
| 2005/0131349 A1 | 6/2005 | Albrecht et al. |
| 2005/0154355 A1 | 7/2005 | Gross et al. |
| 2005/0159765 A1 | 7/2005 | Moutafis et al. |
| 2005/0171467 A1 | 8/2005 | Landman |
| 2005/0261553 A1 | 11/2005 | Swain et al. |
| 2006/0020165 A1 | 1/2006 | Adams |
| 2006/0069306 A1 | 3/2006 | Banik et al. |
| 2006/0129098 A1 | 6/2006 | Hart et al. |
| 2006/0135851 A1 | 6/2006 | Yamazaki |
| 2006/0149135 A1 | 7/2006 | Paz |
| 2006/0173244 A1 | 8/2006 | Boulais et al. |
| 2006/0224121 A1 | 10/2006 | Hart et al. |
| 2006/0224164 A1 | 10/2006 | Hart et al. |
| 2006/0229565 A1 | 10/2006 | Dennis et al. |
| 2006/0293559 A1 | 12/2006 | Grice et al. |
| 2007/0005087 A1 | 1/2007 | Smith et al. |
| 2007/0027360 A1 | 2/2007 | Mitsuya |
| 2007/0027453 A1 | 2/2007 | Hart et al. |
| 2007/0088275 A1 | 4/2007 | Stearns et al. |
| 2007/0088277 A1 | 4/2007 | McGinley et al. |
| 2007/0191759 A1 | 8/2007 | Stoller et al. |
| 2007/0225566 A1 | 9/2007 | Kawanishi |
| 2007/0229954 A1 | 10/2007 | Bral |
| 2007/0255106 A1 | 11/2007 | Kawanishi |
| 2007/0282253 A1 | 12/2007 | Sasaki |
| 2007/0299310 A1 | 12/2007 | Phillips |
| 2008/0009797 A1 | 1/2008 | Stellon et al. |
| 2008/0081948 A1 | 4/2008 | Weisenburgh et al. |
| 2008/0249475 A1 | 10/2008 | Albrecht et al. |
| 2008/0255424 A1 * | 10/2008 | Durgin et al. ................. 600/156 |
| 2008/0269696 A1 | 10/2008 | Exline et al. |
| 2009/0093682 A1 | 4/2009 | Izzo et al. |
| 2009/0137943 A1 | 5/2009 | Stearns et al. |
| 2009/0192444 A1 | 7/2009 | Albrecht et al. |
| 2009/0221960 A1 | 9/2009 | Albrecht et al. |
| 2009/0234193 A1 | 9/2009 | Weisenburgh, II et al. |
| 2009/0234293 A1 | 9/2009 | Albrecht et al. |
| 2009/0240204 A1 | 9/2009 | Taylor et al. |
| 2009/0264703 A1 | 10/2009 | Pribanic |
| 2009/0270681 A1 | 10/2009 | Moreno et al. |
| 2009/0270685 A1 | 10/2009 | Moreno et al. |

(56) References Cited

U.S. PATENT DOCUMENTS

| | | |
|---|---|---|
| 2009/0270813 A1 | 10/2009 | Moreno, Jr. et al. |
| 2009/0270817 A1 | 10/2009 | Moreno et al. |
| 2009/0281478 A1 | 11/2009 | Duke |
| 2009/0314422 A1 | 12/2009 | Racenet et al. |
| 2010/0022958 A1 | 1/2010 | Moreno, Jr. et al. |

FOREIGN PATENT DOCUMENTS

| | | |
|---|---|---|
| EP | 664101 A1 | 7/1995 |
| EP | 721763 | 7/1996 |
| EP | 920276 | 6/1999 |
| EP | 1046371 | 10/2000 |
| EP | 1161175 | 12/2001 |
| EP | 1210904 A2 | 6/2002 |
| EP | 1714608 | 10/2006 |
| EP | 1852056 | 11/2007 |
| EP | 1911392 A2 | 4/2008 |
| GB | 2298906 A | 9/1996 |
| JP | 57-089840 A | 6/1982 |
| JP | 59-028939 A | 2/1984 |
| JP | 63-246133 A | 10/1988 |
| JP | 05103752 A * | 4/1993 |
| JP | 03-136630 B2 | 2/2001 |
| JP | 2001204732 | 7/2001 |
| JP | 2001258824 | 9/2001 |
| JP | 2001286435 | 10/2001 |
| JP | 2002065586 | 3/2002 |
| JP | 2002119465 | 4/2002 |
| JP | 2002177205 | 6/2002 |
| JP | 2002191546 | 7/2002 |
| JP | 2004-313283 A | 11/2004 |
| JP | 2005253543 A * | 9/2005 |
| JP | 2006-075238 A | 3/2006 |
| JP | 2009261923 A | 11/2009 |
| WO | 9703592 | 6/1997 |
| WO | 9809673 A1 | 3/1998 |
| WO | 0053079 | 6/2000 |
| WO | 0160239 | 8/2001 |
| WO | 0189371 | 11/2001 |
| WO | 02091911 | 11/2002 |
| WO | 2005009227 | 2/2005 |
| WO | 2005030293 A2 | 4/2005 |
| WO | 2007089719 | 8/2007 |

OTHER PUBLICATIONS

Japanese Office Action for Application No. 2009-164371 issued May 28, 2013 (5 Pages).

* cited by examiner

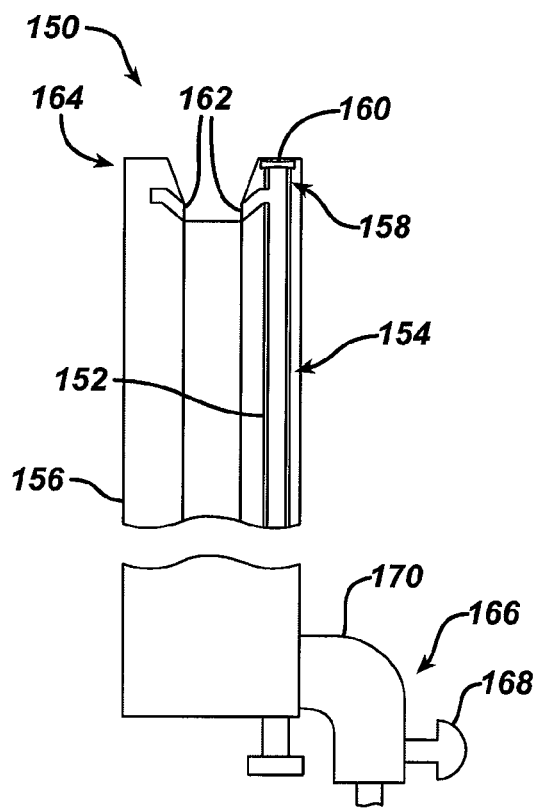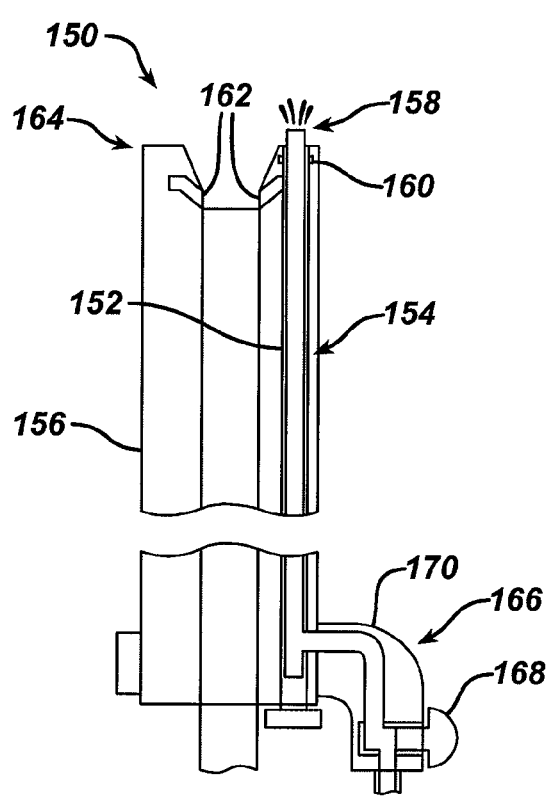

METHODS AND DEVICES FOR MAINTAINING VISIBILITY AND PROVIDING IRRIGATION AND/OR SUCTION DURING SURGICAL PROCEDURES

FIELD OF THE INVENTION

The present invention relates to methods and devices for performing surgical procedures, and in particular to methods and devices for maintaining visibility and providing irrigation and/or suction during surgical procedures.

BACKGROUND OF THE INVENTION

During laparoscopic surgery, one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. During such procedures, a scoping device, such as an endoscope or laparoscope, is inserted through one of the trocars to allow a surgeon to view the operative field on an external monitor coupled to the scoping device.

Scoping devices are often inserted and removed through a trocar multiple times during a single surgical procedure, and during each insertion and each removal a scope can encounter fluid that can adhere to the scope's lens and fully or partially impede visibility through the lens. During some surgical procedures, fluid irrigation is provided to a surgical site, which can increase an amount of fluid present that can potentially impede visibility through the lens. Furthermore, a scope can draw fluid from inside or outside a patient's body into the trocar, where the fluid can be deposited within the trocar until the scope or other instrument is reinserted through the trocar. Upon reinsertion, fluid can adhere to the scope's lens. The scope's lens thus needs to be cleaned to restore visibility, often multiple times during a single surgical procedure. With limited access to a scope in a body, each lens cleaning can require removing the scope from the body, cleaning the scope lens of fluid, and reintroducing the scope into the body. Such lens cleaning is a time-consuming procedure that also increases the chances of complications and contamination through repeated scope insertion and removal.

Accordingly, there is a need for methods and devices for providing irrigation and/or suction to a surgical site and maintaining clear visibility through a lens of a scoping device during a surgical procedure.

SUMMARY OF THE INVENTION

The present invention generally provides methods and devices for delivering irrigation and/or suction to a surgical site and maintaining clear visibility through a lens of a scoping device during a surgical procedure. In one embodiment, a surgical device is provided that includes an annular sheath configured to be disposed in a body cavity and to receive a surgical instrument in a lumen thereof, and a fluid conduit. The sheath also has a passageway having a proximal opening and a distal opening and configured to allow fluid to flow therethrough. The fluid conduit is at least partially located in a distal portion of the sheath and configured to be movable when the sheath is disposed in a body cavity between at least two positions to change a location of the distal opening of the passageway. For example, a first location of the distal opening can be in a distal end of the sheath and a second location of the distal opening can be proximal to the distal end of the sheath.

A variety of surgical instruments can be disposed in the lumen of the sheath, e.g., a scope having a viewing element at a distal end of the scope.

The fluid conduit can have a variety of configurations. For example, the fluid conduit can be in a first position effective to direct fluid flowing through the passageway substantially toward the lumen, and in a second position to direct fluid flowing through the passageway away from the lumen and substantially toward a surgical field. For another example, the fluid conduit in at least one position can allow fluid to be directed through the passageway in a direction substantially aligned with a longitudinal axis of the passageway. In some embodiments, the fluid conduit can selectively allow for fluid irrigation through the passageway and for fluid suction through the passageway.

In an exemplary embodiment, the fluid conduit includes an axially adjustable arm. The arm can have a variety of configurations. For example, the arm can be movable between a first position where a distal end of the arm is proximal to a distal end of the sheath and a second position where the distal end of the arm is distal to the distal end of the sheath. The arm can be movable in a variety of ways, such as with an actuator coupled to a proximal portion of the arm, wherein manipulation of the actuator is effective to move the arm between at least two positions. In some embodiments, the surgical device includes a self-sealing element disposed at a distal end of the sheath, and the arm can be movable between a position proximal to the self-sealing element and a position distal to the self-sealing element.

In another exemplary embodiment, the fluid conduit includes a movable ring disposed at the distal portion of the sheath. The ring can have a variety of configurations. For example, the ring can be located distal to a distal end of a surgical instrument attached to the sheath. For another example, the ring in a first rotated position can allow fluid to flow toward the lumen of the sheath through a distal opening of the passageway proximal to a distal end of the sheath, and the ring in a second rotated position can allow fluid to flow away from the sheath through the distal opening of the passageway at the distal end of the sheath. In some embodiments, the ring in the first rotated position can prevent fluid flow through the distal opening of the passageway away from the distal end of the sheath, and the ring in the second rotated position can prevent fluid flow through the distal opening of the passageway proximal to the distal end of the sheath.

In another embodiment, a surgical device includes a fluid conduit and an annular sheath having first and second passageways extending therethrough. The first passageway can receive a surgical instrument, and the second passageway can allow fluid to flow therethrough. The fluid conduit can move between a first position that allows a distal opening of the second passageway to be substantially directed toward a distal end of a surgical instrument disposed in the first passageway and a second position that allows the distal opening of the second passageway to be substantially directed away from a distal end of the sheath and into a body cavity. In some embodiments, the fluid conduit can be at least partially located proximate to a distal portion of the sheath.

In other aspects, a surgical method is provided. The method includes passing a sheath, having a surgical instrument disposed in a lumen thereof and having a fluid passageway extending therethrough, into a body cavity. A distal end of the surgical instrument is located proximal to a distal end of the sheath, and a fluid conduit that is at least partially located in a distal portion of the sheath can be movable between at least two positions to change a location of a distal opening of the fluid passageway. The method can have any number of variations. For example, passing the sheath into a body cavity can include passing the sheath through an introducer device having a working channel extending into a body cavity. In some embodiments, the fluid conduit can be movable to expose a distal opening of the fluid passageway effective to selectively irrigate and suction a site distal to the sheath. As another example, the fluid conduit can be movable to expose a distal opening of the fluid passageway effective to selectively irrigate and suction a distal end of a surgical instrument disposed in the lumen of the sheath.

BRIEF DESCRIPTION OF THE DRAWINGS

The invention will be more fully understood from the following detailed description taken in conjunction with the accompanying drawings, in which:

FIG. 9 is a partial cross-sectional view of yet another embodiment of a surgical device including a handpiece, and a sheath having an adjustable arm disposed in the sheath and positioned in a first position;

FIG. 10 is a partial cross-sectional view of the surgical device of FIG. 9 with the adjustable arm disposed in the sheath and positioned in a second position;

DETAILED DESCRIPTION OF THE INVENTION

Figure 1:
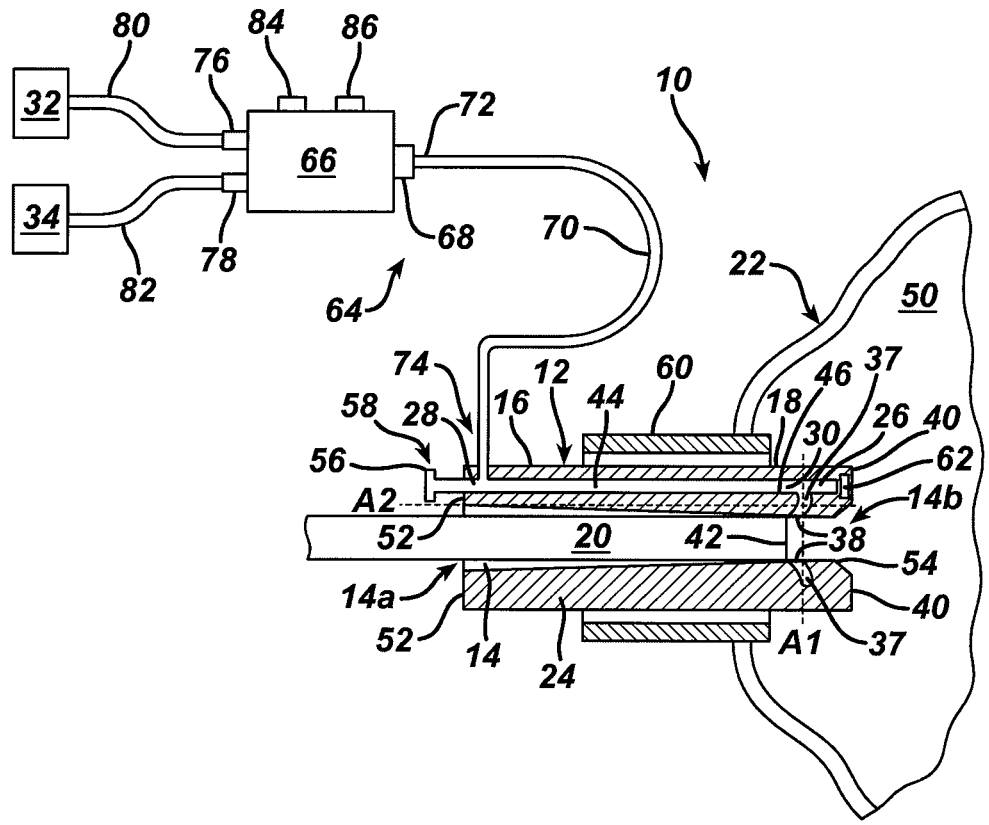
FIG. 1 is a partial cross-sectional view of one embodiment of a surgical device including a handpiece, and a sheath extending into a body cavity and having an adjustable arm disposed in the sheath and positioned in a first position.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A person skilled in the art will appreciate that while the methods and devices are described in connection with endoscopic procedures, the methods and devices disclosed herein can be used in numerous surgical procedures and with numerous surgical instruments. By way of non-limiting example, the devices can be used in laparoscopic procedures, in which the device is introduced percutaneously. The methods and devices can also be used in open surgical procedures. Furthermore, a person skilled in the art will appreciate that the methods and devices disclosed herein can be used with numerous rigid and/or flexible surgical instruments. By way of non-limiting example, the surgical instrument can be a scope, e.g., an endoscope, a laparoscope, a colonoscope, an arthroscope, a gastroscope, etc., and any other type of surgical device that has a distal end that can be disposed in a body cavity and that has a viewing element configured to allow viewing of an image, such as a still or video image on a monitor or through an eyepiece.

A person skilled in the art will appreciate that the term "fluid" as used herein is intended to include any substance that, when on a surgical instrument, can adversely affect the functioning of the instrument or a surgeon's ability to use it. Fluids include any kind of bodily fluid, such as blood, and any kind of cleaning fluid introduced during a surgical procedure, such as saline or air. Fluids also include fluid/solid mixtures or fluids with particles (such as pieces of tissue) suspended or located therein, as well as viscous materials and gases. A person skilled in the art will also appreciate that the term "viewing element" as used herein is intended to encompass any one or more elements (e.g., a lens, a sensor, etc.) configured to allow for any type of visualization through still, moving, or other visual images and that the term "body cavity" as used herein is intended to encompass any internal body area, e.g., the abdominal cavity, the oral cavity, a body lumen, etc. A person skilled in the art will further appreciate that cleaning a distal end of a surgical instrument as discussed herein is intended to include cleaning at least a portion of a distal end of a surgical instrument disposed in a sheath and/or a viewing element disposed at the surgical instrument's distal end.

Various exemplary methods and devices are provided for providing irrigation and/or suction to a surgical site and maintaining clear visibility through a lens of a scoping device during a surgical procedure. In an exemplary embodiment, methods and devices can allow for a surgical instrument to maintain visibility during a surgical procedure using a fluid conduit coupled to the surgical instrument. Generally, a surgical device can include a sheath having at least one lumen extending therethrough configured to allow a surgical viewing instrument to be removably or fixedly disposed therein. The sheath can also have a passageway extending therethrough configured to allow fluid to flow therethrough. The fluid conduit can be removably coupled to or integrally formed in the sheath that is disposable around the surgical instrument such that the fluid conduit can be inserted into and withdrawn from a body cavity simultaneously with the surgical instrument disposed in the sheath. The fluid conduit can be configured to be movable between positions that can allow alternative directions of fluid flow toward and/or away from a viewing element on the surgical instrument to help clean the viewing element and fluid flow away from the viewing element and toward a surgical field in a body cavity to help cleanse the surgical field.

The fluid conduit can thus help clean the viewing element and/or help wash away fluid from a body cavity in which the surgical instrument's viewing element is disposed, thereby helping to maintain acceptable visual clarity through the viewing element. The surgical instrument can therefore be less likely to require withdrawal from the body for replacement with another, clean surgical instrument and/or for cleaning or replacement of the viewing element. In this way, a surgical procedure is less likely to be interrupted one or more times to address a visually impeded viewing element, thereby reducing the time for the surgical procedure. By cleaning a surgical instrument's distal end while the surgical instrument is disposed in the body, the surgical instrument can substantially remain in a desired position near patient tissue of interest, and the surgeon need not take additional time to maneuver the surgical instrument back into desired position following the instrument's cleaning and/or replacement with another surgical instrument. Reducing the need to remove the surgical instrument out of the body, such as through an introducer device used to introduce the surgical instrument into or remove the surgical instrument from a body cavity, can also reduce chances of the surgical instrument drawing fluid into the introducer device that could obscure the viewing element's viewing path during its passage through the introducer device and/or upon the surgical instrument's reinsertion (or other surgical instrument's insertion) into the introducer device. Furthermore, the fluid conduit in one or both of its alternate positions can allow fluid be to suctioned away from adjacent the viewing element or from a surgical site distally beyond the viewing element, such as smoke or mist within a body cavity, which can help remove fluid that could potentially obscure vision through the viewing element or could otherwise adversely affect a surgical procedure. Providing fluid suction and fluid irrigation using the same sheath and fluid conduit system associated with a surgical instrument can also help reduce the amount of instrumentation needed during a surgical procedure.

FIGS. 1-5 illustrate one exemplary embodiment of surgical device 10 including a fluid conduit, e.g., an extendable arm 44, coupled to an annular sheath 12. The surgical device 10 can be formed from any type and any combination of materials, preferably fluid-impermeable, preferably rigid and/or semi-rigid, and preferably biocompatible materials. The surgical device 10 can be configured with a fluid conduit as discussed below but otherwise be configured similar to surgical devices described in U.S. Patent Publication No. 2008/0081948 filed Oct. 3, 2006 entitled "Apparatus For Cleaning A Distal Scope End Of A Medical Viewing Scope" and in U.S. patent application Ser. No. 12/047,474 filed Mar. 13, 2008 entitled "Apparatus For Keeping Clean A Distal Scope End Of A Medical Viewing Scope," which are incorporated by reference in their entireties. Generally, the surgical device 10 can include the annular sheath 12 having proximal and distal portions 16, 18 and having a lumen 14 with open proximal and distal ends 14a, 14b extending therethrough. The lumen 14 can be configured to receive a surgical instrument such as an endoscope 20 disposed at least partially therein. The sheath 12, before and/or after the endoscope 20 has been disposed within the lumen 14, can be configured to be directly inserted into a patient 22 or be inserted into the patient 22 through a working channel of an introducer device, e.g., a trocar 60, extending into the patient's body cavity 50.

Figure 4:
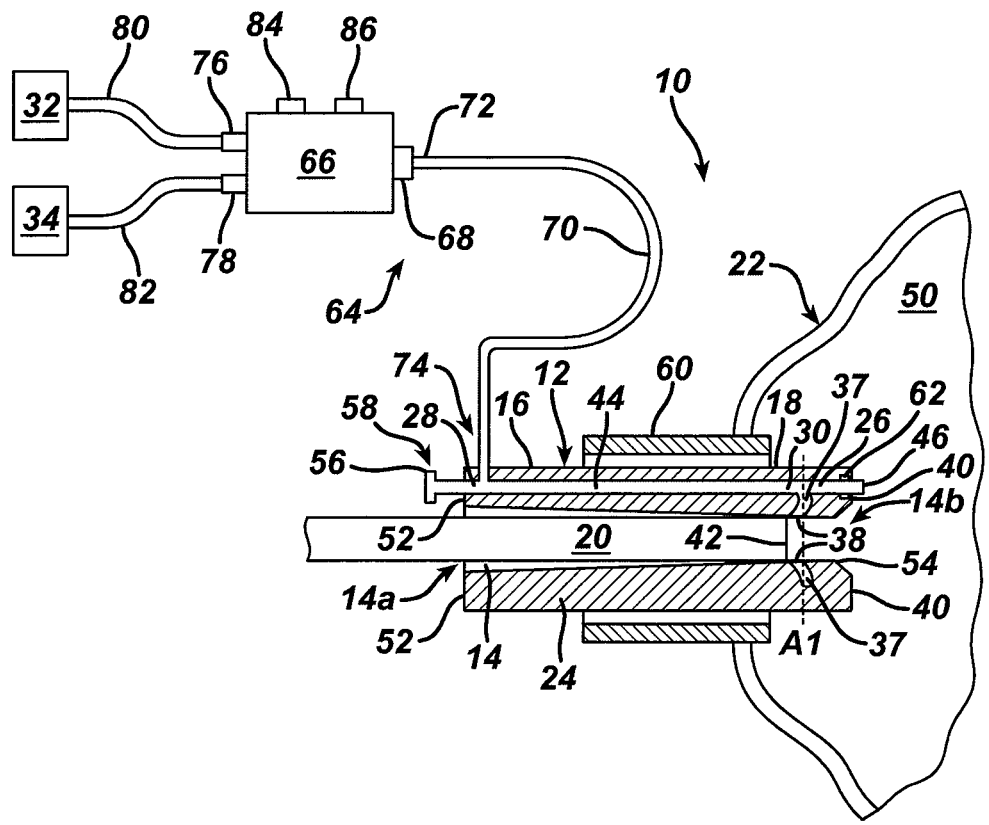
FIG. 4 is a partial cross-sectional view of the surgical device of FIG. 1 with the adjustable arm disposed in the sheath and positioned in a second position.
Figure 5:
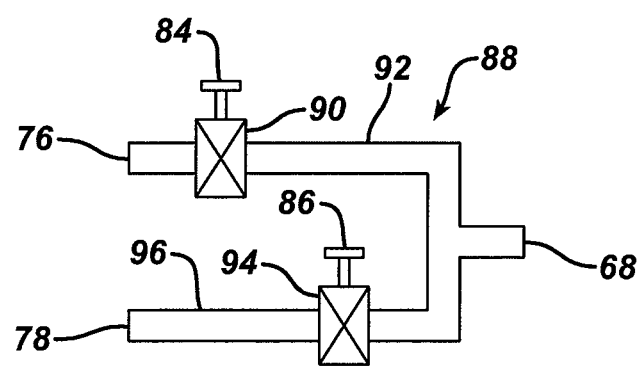
FIG. 5 is schematic diagram of the handpiece of FIG. 1.

The endoscope 20 can be fixedly attached to the sheath 12, or the endoscope 20 can be removably coupled to the sheath 20, such as by slidably disposing the endoscope 20, distal end 42 first, into the lumen 14 through the sheath's proximal portion 16. The endoscope's distal end 42 has an outside diameter. An inside diameter of a tubular wall 24 at the sheath's distal portion 18 can be less than the outside diameter of the endoscope's distal end 42 to help hold the endoscope 20 within the lumen 14 and to help prevent the endoscope 20 from sliding distally beyond the sheath's distal end 40. As shown in FIGS. 1 and 4, the endoscope's distal end 42 can make a press fit with the sheath 12 at the sheath's distal portion 18. The press fit can be accomplished in any way appreciated by a person skilled in the art, such as by varying the diameter of the lumen 14 such that the inside diameter of the tubular wall 24 tapers from the sheath's proximal end 52 to the sheath's distal end 40 or tapers along any portion thereof. The endoscope 20 can be coupled to the sheath 12 in any way appreciated by a person skilled in the art, e.g., by using an elastomeric sheath, a compression fitting, an elastomeric O-ring attached to the sheath 12 proximate the sheath's distal end 40 and configured to attachingly engage the endoscope 20 which has been inserted into the sheath's proximal end 52, etc.

As mentioned above, the sheath 12 has a tubular wall 24, which has inside and outside diameters and contains a passageway 26 between the inside and outside diameters. The inside diameter of the tubular wall 24 is defined by the diameter of the lumen 14, while the outside diameter of the tubular wall 24 is defined by an outside diameter of the sheath 12. The passageway 26 has open proximal and distal portions 28, 30 configured to allow a fluid to flow therethrough. At least between the proximal and distal portions 28, 30, the passageway 26 can be substantially aligned with a longitudinal axis A2 of the sheath 12. The proximal portion 28 of the passageway 26 has an opening that can be fluidly coupled to at least one of a fluid irrigation source 32 and a fluid vacuum source 34 as discussed further below. The distal portion 30 of the passageway 26 has at least two openings that can alternatively serve as a distal end opening of the passageway 26 through adjustment of a fluid conduit as discussed further below.

Figure 2:
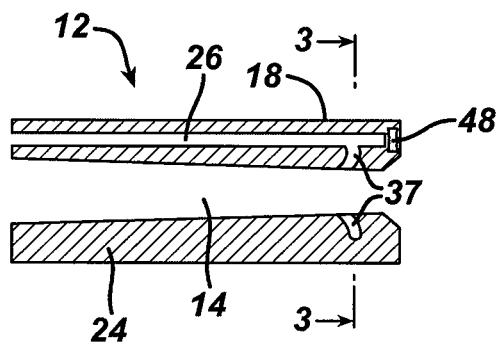
FIG. 2 is a cross-sectional view of the sheath of FIG. 1 outside a body cavity.
Figure 3:
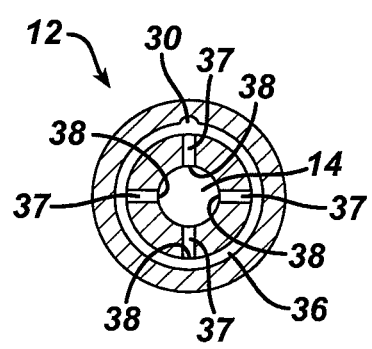
FIG. 3 is a cross-sectional view of a distal portion of the sheath of FIG. 2.

The distal portion 18 of the sheath 12 has an annular manifold 36, illustrated in FIG. 3, which includes at least one proximal orifice 38 located in the distal portion 18 of the sheath 12 and proximal to a distal end 40 of the sheath 12 and preferably directed substantially toward the lumen 14, and more preferably directed substantially toward a position of a distal end 42 of the endoscope 20 disposed in the lumen 14. In this way, at least some of the time, fluid flowing through the passageway 26 can be configured to be in fluid communication with the lumen 14 and/or with the endoscope's distal end 42 in the lumen 14. In this way, fluid flowing out of the proximal orifice 38 (e.g., flowing in a distal direction through the passageway 26) can clean inside the lumen 14 and/or clean the endoscope's distal end 42, and hence also a viewing element at the endoscope's distal end 42. Similarly, allowing fluid to flow into the proximal orifice 38 (e.g., in a proximal direction through the passageway 26) can draw fluid away from inside the lumen 14 and/or from the endoscope's distal end 42. Two proximal orifices 38 are shown in FIGS. 1, 2, and 4, and four proximal orifices 38 are shown in FIG. 3, although the passageway 26 can have any number of proximal orifices, and each proximal orifice can optionally include a plurality of circumferentially spaced apart orifices. The annular manifold 36 can have a volume greater than a total volume of passages 37 between the manifold 36 and each of the proximal orifices 38. The passages 37 are portions of the passageway 26 extending to the proximal orifices 38 such that the passages 37 are portions of the passageway 26 prevented from having fluid flow therein when the arm 44 is in the second, distal position. A plurality of proximal orifices 38 can be substantially axially aligned along a cross-sectional axis A1 of the sheath 12, as shown in FIGS. 1, 2, and 4, or one or more proximal orifices 38 can be substantially non-axially aligned from any one or more other proximal orifices 38 such that at least two of the orifice(s) 38 are axially aligned with different cross-sectional axes of the sheath 12. The passages 37 are preferably substantially parallel to the cross-sectional axis A1, although each of the passages 37 can be linear or non-linear (same or different from any of the other passages 37). The sheath's distal portion 18 can have a circumferentially inner surface 54 containing the proximal orifice 38. Fluid can tend to adhere to the circumferentially inner surface 54, thereby helping to keep fluid off and away from the endoscope's distal end 42 and outside a viewing path of a viewing element at the endoscope's distal end 42. The circumferentially inner surface 54 of the sheath's distal portion 18 can longitudinally extend from the sheath's distal end 40 to the endoscope's distal end 42, as seen in FIG. 1.

The passageway 26 can be configured to receive a fluid conduit, e.g., the extendable arm 44, disposed therein through which fluid can flow. The arm 44 has an outer diameter that is less than the diameter of the passageway 26 such that the arm 44 can slidably move within the passageway 26. The arm 44 can be rigid and/or flexible, but the arm 44 is preferably rigid enough to help move the arm 44 through the passageway 26 and to help penetrate a seal 62 as discussed below. However, the arm 44 is also preferably flexible enough to help the arm 44 navigate any curves, bens, twists, etc. in the passageway 26. The arm 44 preferably has a constant cross-sectional area, at least in a fluid-carrying portion of the arm 44 configured to be disposable within the passageway 26, to help reduce flow losses and provide better response times for fluid flowing through the arm 44. The arm 44 also preferably has a cross-sectional shape that substantially matches the passageway's cross-sectional shape, e.g., circular, elliptical, crescent-shaped, etc., to help smoothly pass the arm 44 through the passageway 26.

When the arm 44 is in a first, proximal position, shown in FIG. 1, an open distal end 46 of the extendable arm 44 is located proximal to the passageway's proximal orifice 38 such that fluid flowing through the arm's distal end 46 is in fluid communication with the proximal orifice 38 such that fluid can flow through the passageway 26 and the proximal orifice 38. The arm 44 can be axially adjustable, e.g., adjustable substantially parallel to the longitudinal axis A2. Advancing the arm 44 distally can advance at least a portion of the arm 44 including at least the arm's distal end 46 through the seal 62 located between the proximal orifice 38 and the sheath's distal end 40. The arm's distal end 46 can be substantially linear, as shown in FIGS. 1 and 4, or the distal end 46 can be non-linear, e.g., curved, conical, etc., to help the arm 44 "break" the seal 62 and/or to help increase a rate or pressure of fluid flowing distally through the distal end 46. When the arm 44 is distally advanced through the seal 62 and in a second, distal position, shown in FIG. 4, the arm's distal end 46 is located distal to the proximal orifice 38 such that fluid is prevented from flowing through the proximal orifice 38 and instead can flow through the arm's distal end 46 and through at least one distal orifice 48 in the sheath 12. Similar to that discussed above regarding the proximal orifice 38, the passageway 26 can include any number of distal orifices, and each distal orifice can optionally include a plurality of circumferentially spaced apart orifices. In the second, distal position, at least a portion of the arm 44 can extend distally beyond the sheath's distal end 40 such that fluid flowing through the passageway 26 can flow through the arm 44 and does not contact the passageway's inner wall, as shown in FIG. 4. Alternatively, the arm 44 can be advanced through the seal 62 a distance that allows the seal 62 to be "broken" or penetrated but that keeps the arm's distal end 46 contained within the sheath 12, e.g., located proximal to the sheath's distal orifice 48 and between the seal 62 and the sheath's distal end 40.

The sheath 12 can include a stop element in its distal portion 18 to help prevent the arm 44 from being distally advanced beyond the sheath's distal end 40 and to help reduce chances of the arm 44 interfering with a surgical site beyond the sheath's distal end 40. Non-limiting examples of the stop element include a fluid-permeable mesh disposed over the sheath's distal orifice 48, a lip around the sheath's distal orifice, a diameter of the passageway 26 in at least a portion of the passageway 26 distal to the seal 62 that is smaller than a diameter of the arm 44 similar to that described above regarding the endoscope 20 in the lumen 14, etc. However, in some surgical procedures it can be desirable to allow the arm 44 to extend beyond the sheath's distal end 40, as illustrated in the second position in FIG. 4, so fluid can be more directly irrigated into or suctioned from a surgical site. The distal orifice 48 is preferably formed in the sheath's distal end 40 to maximize flow of fluid beyond the sheath's distal end 40, but the distal orifice 48 can be at any location in the sheath 12 that can allow fluid flowing through the passageway 26 to be in fluid communication with the body cavity 50 in which at least part of the distal portion 18 of the sheath 12 is disposed, e.g., in a side of the sheath 12.

The seal 62 can include any one or more fluid seals alone or in combination as will be appreciated by a person skilled in the art. The seal 62 can include a zero-closure seal and/or an instrument seal, e.g., a duckbill seal, a flapper valve, a flapper door, a gel pad seal, an overlapping multi-layer seal, etc. Preferably, the seal 62 is configured to be self-sealing such that the arm 44 can be distally advanced through the seal 62 to penetrate the seal 62 and can be proximally moved through the seal 62 to "re-seal" the seal 62. In some embodiments, the seal 62 can be configured for one-time use such that distally advancing the arm 44 breaks the seal 62 and proximally moving the arm 44 to a position proximal of the seal 62 does not allow for "re-sealing" of the seal 62.

In some embodiments, the arm 44 can be configured to engage the passageway 26, such as by having corresponding mating threads, grooves, or other engagement mechanism(s) on an inner surface of the passageway 26 and on an outer surface of the arm 44. Such an engagement mechanism can help hold the arm 44 in a desired position within the passageway 26 and/or help guide the arm 44 smoothly through the passageway 26. Alternatively or in addition, the arm 44 can include a locking mechanism, preferably at its proximal end 58 where it can be manipulated outside the patient 22, configured to hold the arm 44 in a desired position within the passageway 26. Non-limiting examples of the locking mechanism include tabs, corresponding depressions and protrusions on the sheath 12 and the arm 44 that allow for successive positions of the arm 44 within the passageway 26, etc.

The arm 44 can be moved between the first and second positions in a variety of ways. In an exemplary embodiment, the arm 44 can be moved by manually manipulating a handle 56 at the arm's proximal end 58. The handle 56 can have any size, shape, and configuration and is preferably configured to at least partially extend outside the patient 22 when at least a portion of the sheath 12 is disposed in the patient's body cavity 50. The handle 56 can be pushed distally to distally advance the arm 44, thereby moving the arm 44 from the first position to the second position. Correspondingly, the handle 56 can be pulled proximally to proximally retract the arm 44, thereby moving the arm 44 from the second position to the first position. A person skilled in the art will appreciate that the arm 44 can be moved between any number of positions before and/or after the first and second positions. The handle 56 can include mechanical and/or electrical components. The handle 56 can be configured to abut the proximal end 52 of the sheath 12 to help prevent the arm 44 from being entirely disposed within the passageway 26. For example, the handle 56 can have a maximum diameter greater than a diameter of the passageway 26, at least at the second lumen's proximal portion 28, so that a distal surface of the handle 56 can abut the sheath's proximal portion 28 without sliding into the passageway 26. In other embodiments, the arm 44 can be configured to move in another way, such as through manipulation of a button, a lever, and/or other control in mechanical and/or electronic communication with the arm 44 such that the arm 44 can move when the control is manipulated, e.g., pushed, pulled, switched, etc.

The device 10 can also include a fluid system 64 configured to provide a fluid irrigation source and/or fluid evacuation source to the sheath 12, and more particularly to the fluid passageway 26 and the arm 44 disposed in the passageway 26. Generally, in an exemplary embodiment, the fluid system 64 can include the irrigation source 32, the vacuum source 34, a handpiece 66 having a fluid outlet 68, and a flexible fluid flow tube 70 having proximal and distal tube ends 72, 74. The distal tube end 74 can be coupled to the sheath 12 to be in fluid communication with the proximal portion 28 of the passageway 26, and more particularly to the arm 44 in the proximal portion 28 of the passageway 26. In this way, fluid flowing through the arm 44 in the passageway 26 can be able to flow through the tube 70 and vice versa. The arm 44 can be coupled to the tube 70 through a sidewall of the sheath 12, as shown in FIGS. 1 and 4. Alternatively, the arm 44 can be coupled to the tube 70 proximal to the proximal end 52 of the sheath 12, such as through the arm's handle 56. The proximal tube end 48 can be coupled to the handpiece 66 to be in fluid communication with the fluid outlet 68. The handpiece 66 includes first and second fluid inlets 76, 78, with the first fluid inlet 76 fluidly coupled, e.g., via first tubing 80, to the irrigation source 32, and the second fluid inlet 78 fluidly coupled, e.g., via second tubing 82, to the vacuum source 34. The irrigation source 32 can include any one or more types of fluid (liquid and/or gas). The vacuum source 34 can provide any one or more of a full vacuum, a partial vacuum, and aspiration. A vacuum provided by the vacuum source 34 is relative to the pressure at the distal opening of the passageway 26, whether the distal opening is located at the proximal orifice 38 or the distal orifice 48. In some embodiments, the vacuum source 34 can be ambient room air when the passageway's distal opening is exposed to a higher pressure within, e.g., the insufflated abdomen of a patient. As will be appreciated by a person skilled in the art, in some embodiments, one or more additives, e.g., an anti-fogging agent such as a surfactant, can be added to fluid in one or more of the sources 32, 34, to fluid flowing through one or both of the tubings 80, 82, and/or through the tube 70. By way of non-limiting example only, the irrigation source 32 can include an operating-room saline bag, the first tubing 80 being fluidly connected to the bag, and the vacuum source 34 can include an operating-room suction canister, the second tubing 82 being fluidly connected to the canister. A bladder can optionally be placed around the saline bag to increase pressure of the irrigation fluid.

The handpiece 66 can be configured to alternatively switch between the irrigation source 32 and the vacuum source 34, such as by using first and second valve buttons 84, 86. In this way, fluid can flow proximally or distally through the passageway 26 to, respectively, provide fluid aspiration and irrigation. Pushing or otherwise actuating the first valve button 84 can fluidly connect the first fluid inlet 76 to the fluid outlet 68, and pushing or otherwise actuating the second valve button 86 can fluidly connect the second fluid inlet 78 to the fluid outlet 46. Although other switching arrangements will be appreciated by a person skilled in the art, in an exemplary embodiment shown in FIG. 5, a "Y" passageway 88 can fluidly connect the first and second fluid inlets 76, 78 to the fluid outlet 68. The first valve button 84 is operatively connected to a first valve 90 disposed in a first arm 92 of the "Y" passageway 88. The second valve button 86 is operatively connected to a second valve 94 disposed in a second arm 96 of the "Y" passageway 88. Such as "Y" passageway configuration can allow for user-selectable fluid flow configurations that allow the fluid outlet 68 to be in fluid communication with one but not the other of the fluid inlets 76, 78 at any given time (or with neither of the fluid inlets 76, 78). Various valve configurations are described in more detail in U.S. Patent Publication No. 2008/0081948 and U.S. patent application Ser. No. 12/047/474, both mentioned above.

Figure 6:
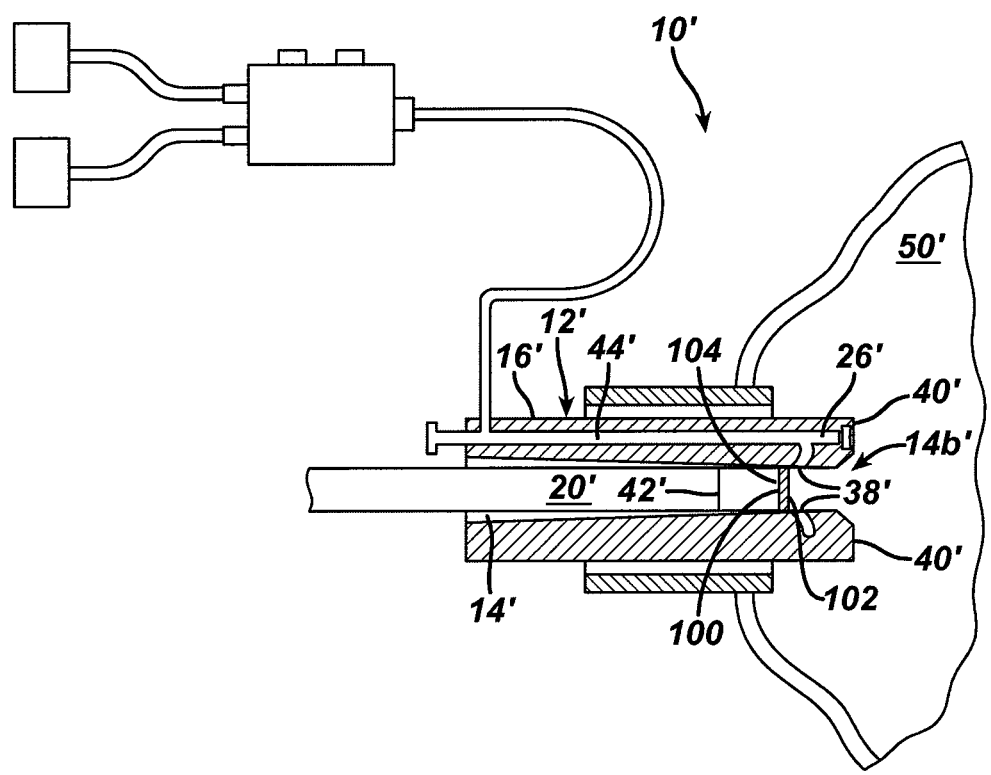
FIG. 6 is a partial cross-sectional view of one embodiment of a surgical device including a handpiece, and a sheath extending into a body cavity and having an adjustable arm and a protective lens disposed in the sheath.

FIG. 6 illustrates another embodiment of a surgical device 10' that can be used to irrigate and/or aspirate a distal end 42' of an endoscope 20' and/or a body cavity 50'. The endoscope 20' is disposed in a lumen 14' of a sheath 12'. Also disposed in the lumen 14' is a protective lens 100 that can attach to the sheath 12', preferably fixedly although it can be removably attached. The lens 100 closes off the sheath 12' proximate to the sheath's distal end 40' by effectively closing off the lumen 14' proximate to the lumen's distal end 14b'. The endoscope 20' is insertable into the sheath's proximal portion 16' with its distal end 42' disposed proximate to the lens 100. The lumen 14' is tapered in this illustrated embodiment, and given the size of the endoscope 20' disposed therein, the endoscope 20' is prevented from contacting the lens 100, but another surgical instrument disposed in the lumen 14' can be configured to contact a proximal surface 104 of the lens 100. In this way, a distal surface 102 of the lens 100 helps protect the endoscope's distal end 42' and be in fluid communication with a proximal orifice 38' of a fluid passageway 26' such that when the proximal orifice 38' defines a distal opening of the passageway 26' based on a position of an arm 44' disposed in the passageway 26', fluid flowing through the proximal orifice 38' can help clean the distal surface 102 of the lens 100. The lens 100 can be optically clear and can be a non-magnifying or a magnifying lens.

Figure 7:
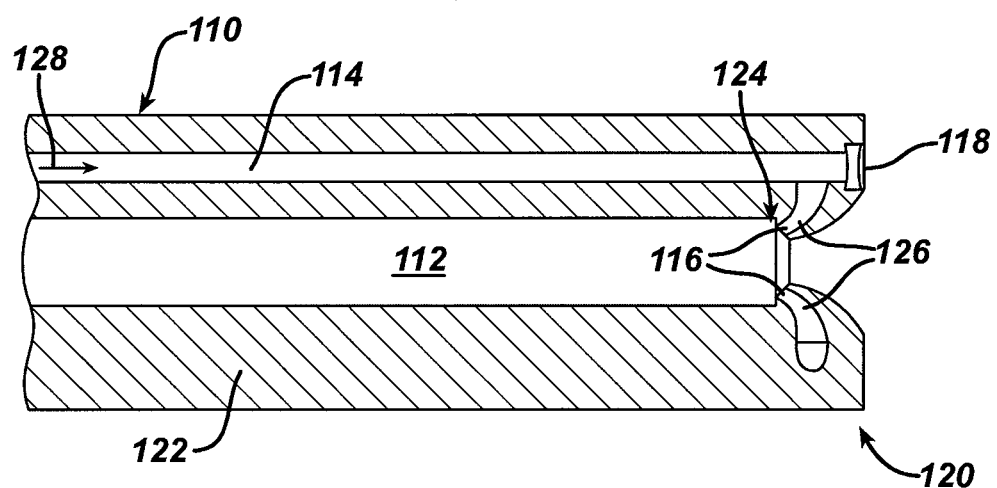
FIG. 7 is a partial cross-sectional view of a distal portion of another embodiment of a surgical device including a sheath and having an adjustable arm disposed in the sheath.

FIG. 7 illustrates another embodiment of an annular sheath 110 having a lumen 112 extending therethrough in which a surgical instrument (not shown) can be disposed. The sheath 110 also has a fluid passageway 114 formed in the sheath's tubular wall 122 through which fluid can flow between a proximal opening of the passageway (not shown) and a distal opening of the passageway 114. The distal opening can either include a proximal orifice 116, which is substantially directed at the distal end 124 of the lumen 112 where a distal end of a surgical instrument can be positioned in the lumen 112, or a distal orifice 118, substantially directed beyond a distal end 120 of the sheath 110. The proximal orifice 116 or the distal orifice 118 can thus be selectively chosen as the passageway's 114 distal opening depending on a position of an extendable arm (not shown) disposed within the passageway 114. A proximal orifice passageway 126 between the sheath's passageway 114 and the proximal orifice 116 can taper, as shown in FIG. 7, to help increase a rate and/or pressure of fluid flowing out of the proximal orifice 116 when fluid is flowing in a distal direction indicated by arrow 128, although the proximal orifice passageway 126 can have any configuration. The proximal orifice 116 has a portion abutting the lumen's distal end 124 and a portion spaced apart from the lumen's distal end 124. A portion of the tubular wall 122 defines the distal end 124 of the lumen 112 such that the tubular wall 122 forms a stop element in the form of a lip or shelf that can contact a distal surface of a surgical instrument disposed within the lumen 112 and prevent further distal movement of the surgical instrument through the sheath 110. The tubular wall 122 can include an annular manifold, discussed above, and the stop element can be a part of the manifold. The lumen 112 and the tubular wall 122 are thereby configured to allow a distal end of a surgical instrument disposed in the lumen 112 to contact the lumen's distal end 124 and abut a portion of the tubular wall 122. In this way, when fluid is configured to flow through the proximal orifice 116, fluid can be irrigated or suctioned substantially to or from the surgical instrument's distal end.

Figure 8:
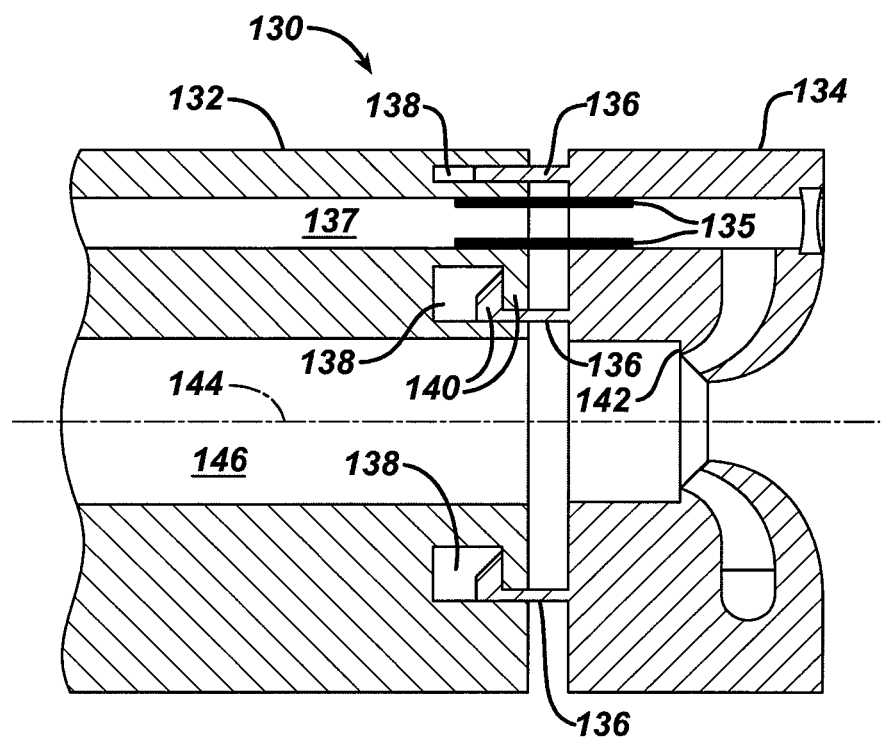
FIG. 8 is a partial cross-sectional view of a distal portion of one embodiment of a surgical device including a sheath having a movable manifold and having an adjustable arm disposed in the sheath.

FIG. 8 illustrates another embodiment of an annular sheath 130 including proximal and distal sections 132, 134. The distal section 134 is coupled to the proximal section 132 and is manually expandable and rotatable with respect to the proximal section 132 of the sheath 130, although in other embodiments the rotation and/or expansion can be mechanically and/or electronically actuated. In an exemplary embodiment, the proximal and distal sections 132, 134 are coupled with a rotatable tongue 136 (rotatable about a central longitudinal axis 144) and an at-least-partially-annular groove 138 arrangement. At least one locking tab 140 formed on each of the proximal and distal sections 132, 134 can abut each other during extension of the distal section 134 with respect to the proximal section 132 to help prevent separation of the distal section 134 from the proximal section 132. A seal member 135 can be coupled to the proximal and distal sections 132, 134 and be disposed in a fluid passageway 137 of the sheath 130 to help fluidly seal the passageway 137 during extension of the distal section 134 so fluid can flow through the passageway 137 between the proximal and distal sections 132, 134. In some embodiments, a distal end of a surgical instrument disposed in a lumen 146 of the sheath 130 can be angled for improved sideways viewing, the distal section can be correspondingly angled, and the rotatable feature can allow rotational alignment of the angled distal section with the angled distal end of the surgical instrument. A stop element 142 at a distal end of the lumen 146 in this embodiment is shown as a portion of the distal section 134. Surgical instruments can vary a small amount (such as one inch) in length, and the extendable and retractable distal section 134 can allow surgical instruments of varying length to be fully inserted in the sheath 130 against the stop element 142.

FIGS. 9 and 10 illustrate another exemplary embodiment of a surgical device 150 including a fluid conduit in the form of an extendable arm 152 disposed in a passageway 154 of an annular sheath 156. FIG. 9 illustrates the arm 152 in a first, distal position where the arm's distal end 158 is disposed proximal to a seal 160 in the passageway 154 such that fluid can flow through a proximal orifice 162. FIG. 10 illustrates the arm 152 in a second, proximal position where the arm 152 has been pushed distally so the arm's distal end 158 has passed distally beyond the seal 160 such that fluid can flow through the arm's distal end 158 and beyond the sheath's distal end 164. Flow of fluid through the arm 152, whether the arm 152 is in the first or second position, can be controlled through manipulation of a trumpet valve 166. The trumpet valve 166 can be coupled to a proximal portion 168 of the sheath 156 to help allow for manipulation of the trumpet valve 166 outside a patient's body when at least a portion of the device 150 is disposed in a patient. As will be appreciated by a person skilled in the art, the trumpet valve 166 can be actuated using a button 168 configured to control flow of fluid through the trumpet valve's handle 170 and hence also through the passageway 154.

Figure 11:
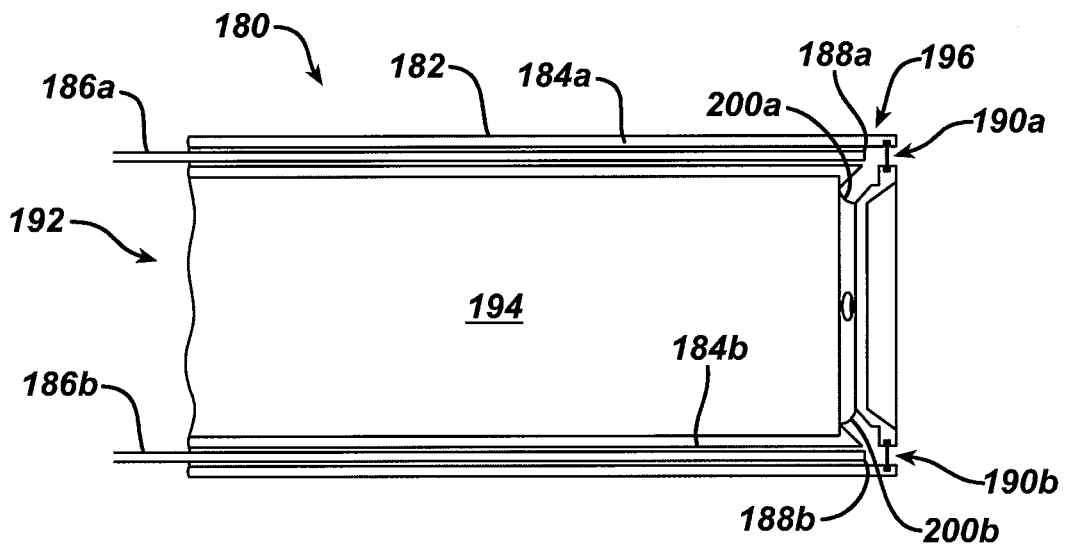
FIG. 11 is a partial cross-sectional view of a distal portion of one embodiment of a surgical device including a sheath and having a plurality of adjustable arms disposed in the sheath with the arms positioned in a first position.
Figure 12:
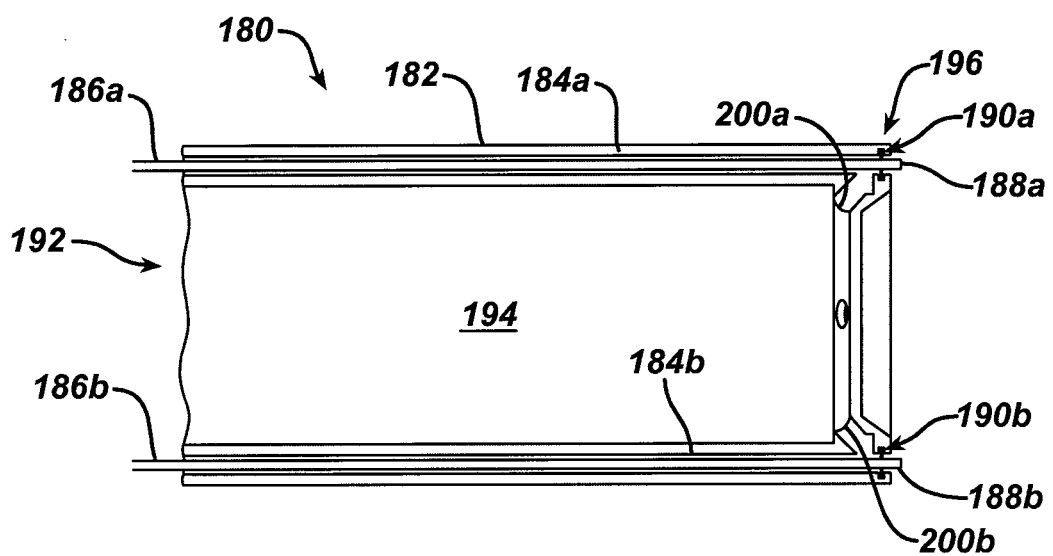
FIG. 12 a partial cross-sectional view of the surgical device of FIG. 11 with the adjustable arms disposed in the sheath and positioned in a second position.
Figure 13:
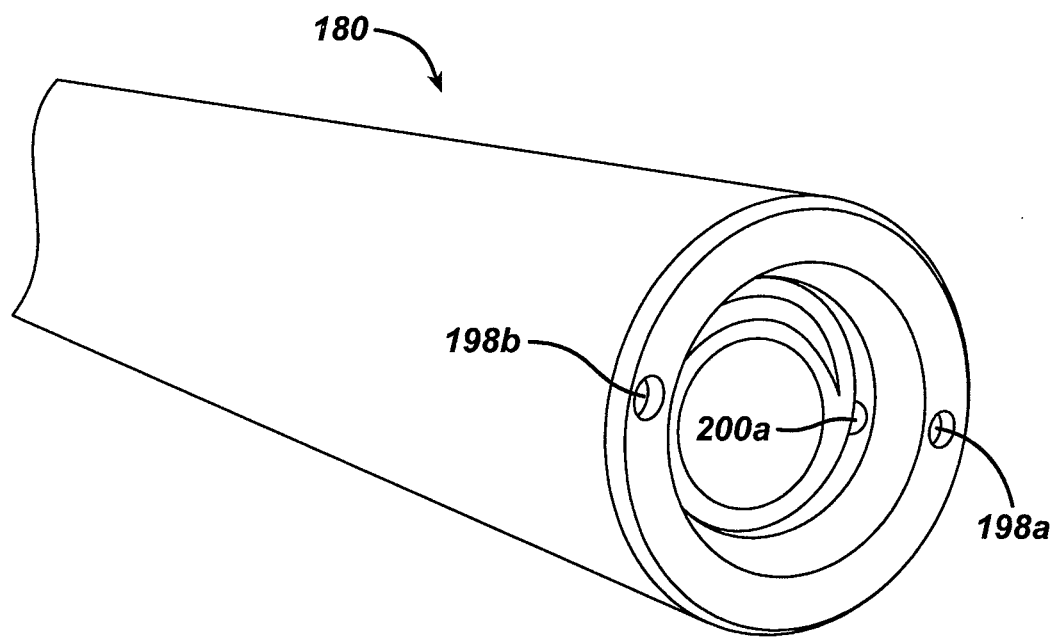
FIG. 13 is a partial perspective view of a distal end of the surgical device of FIG. 11.
Figure 14:
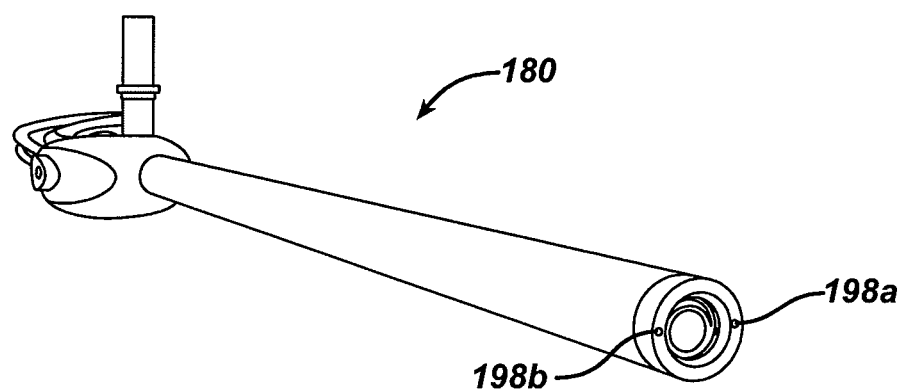
FIG. 14 is a perspective view of the surgical device of FIG. 11.
Figure 15:
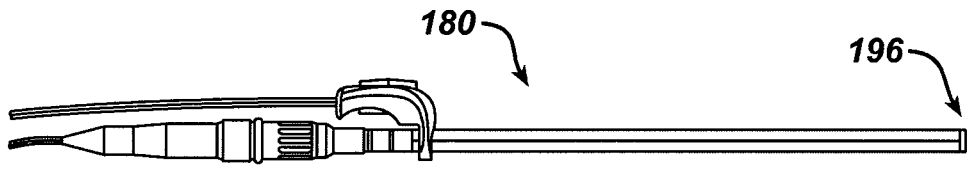
FIG. 15 is a side view of the surgical device of FIG. 14.
Figure 16:
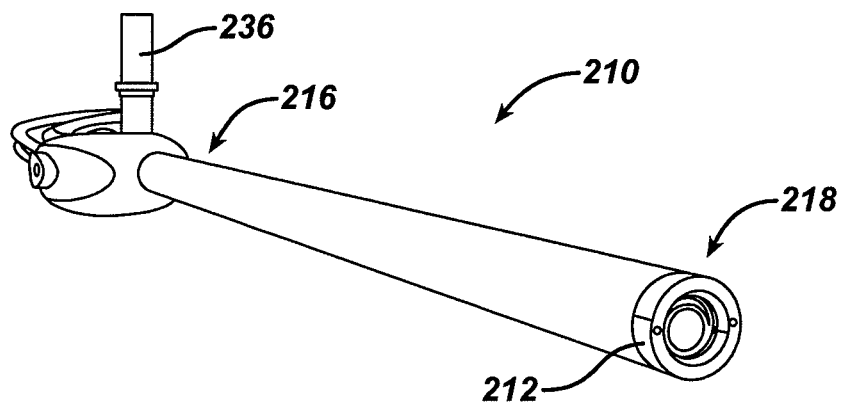
FIG. 16 is a perspective view of one embodiment of a surgical device including a sheath and having a movable ring located at least partially in a distal portion of the sheath.
Figure 17:
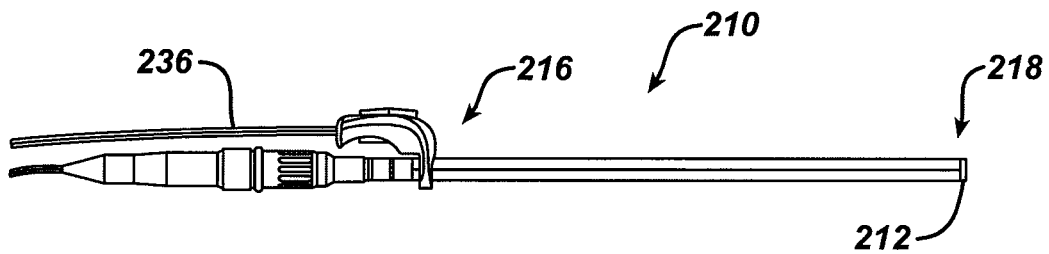
FIG. 17 is a side view of the surgical device of FIG. 16.
Figure 18:
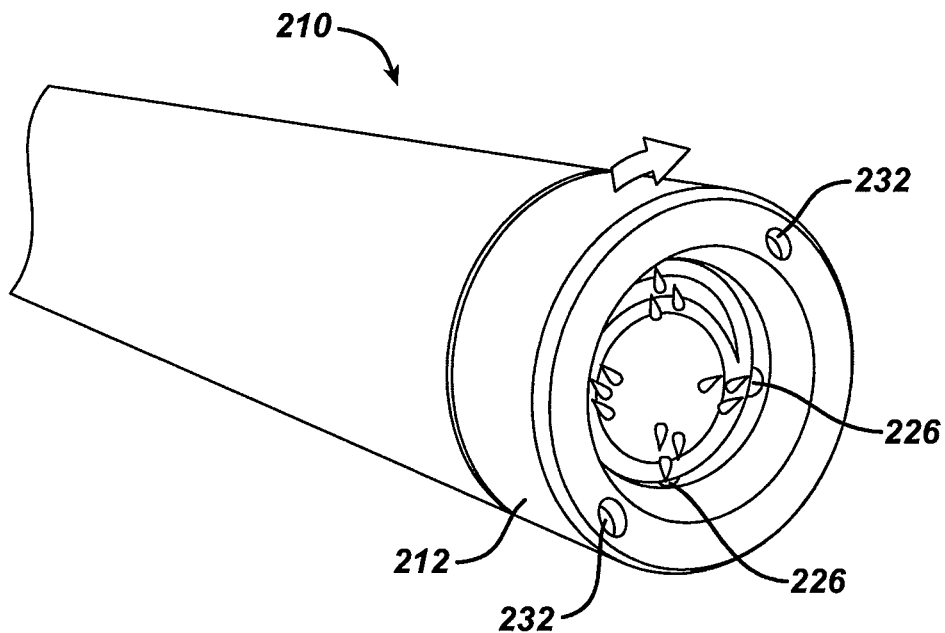
FIG. 18 is a partial perspective view of a distal end of the surgical device of FIG. 16 with the ring in a first position.
Figure 19:
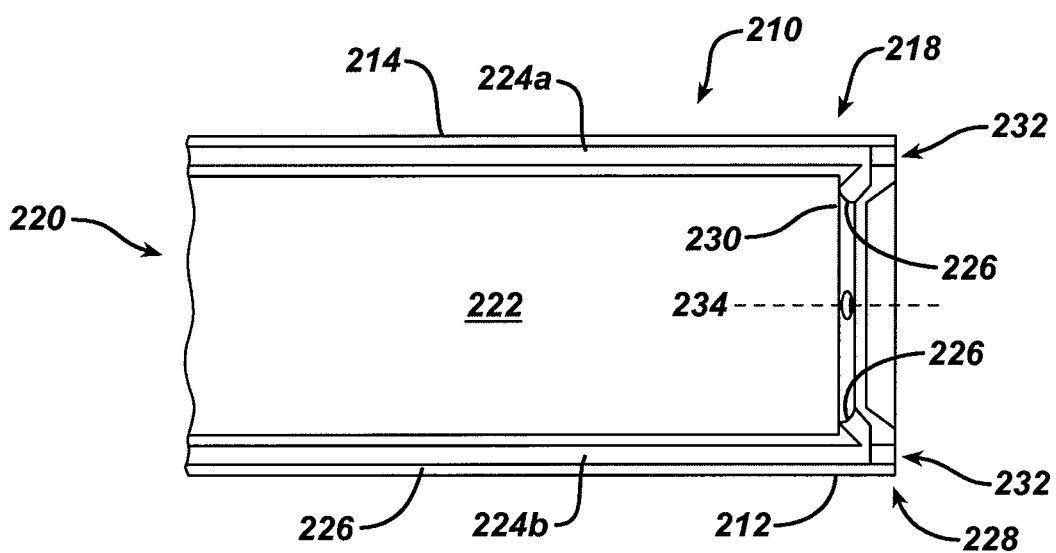
FIG. 19 is a partial cross-sectional view of a distal end of the surgical device of FIG. 16 with the ring in a first position.
Figure 20:
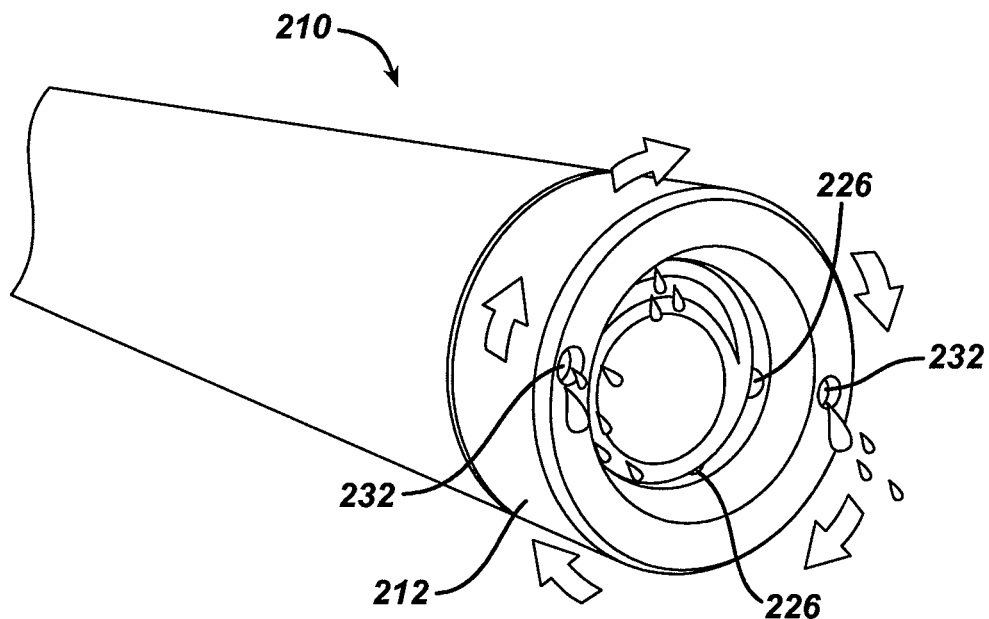
FIG. 20 is a partial perspective view of a distal end of the surgical device of FIG. 16 with the ring in a second position.
Figure 21:
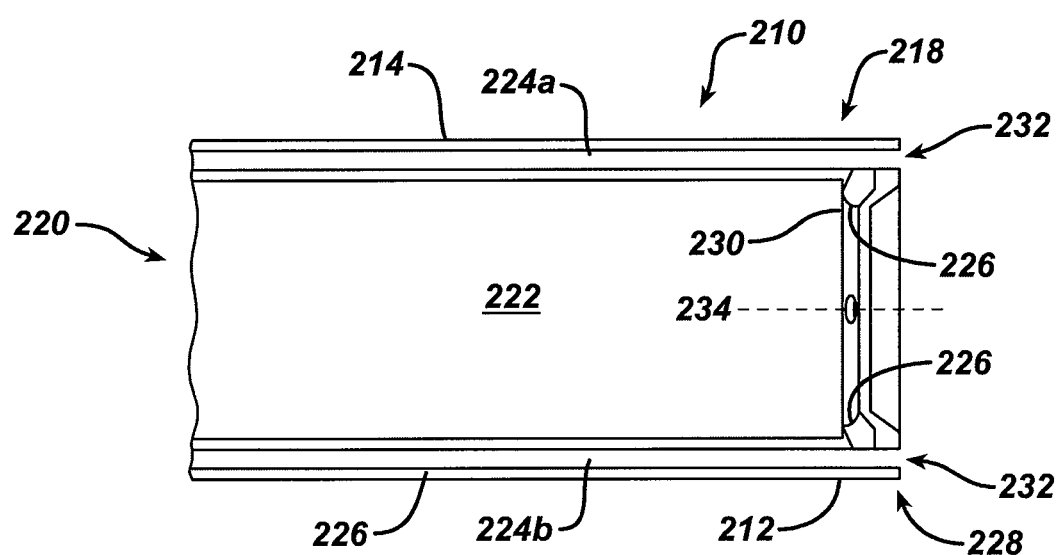
FIG. 21 is a partial cross-sectional view of a distal end of the surgical device of FIG. 16 with the ring in a second position.
Figure 22:
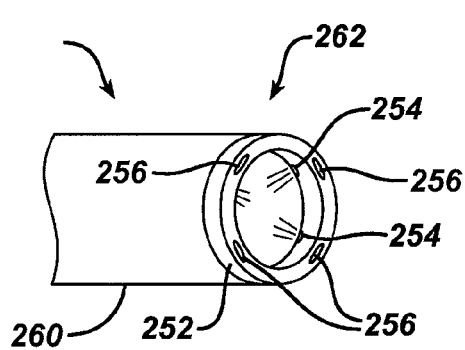
FIG. 22 is a partial perspective view of a distal portion of one embodiment of a surgical device including a sheath and having a movable ring located at least partially in a distal portion of the sheath with the ring positioned in a first position.
Figure 23:
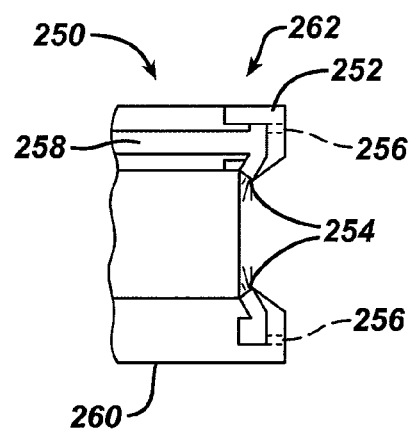
FIG. 23 is a partial cross-sectional view of the surgical device of FIG. 22.

FIGS. 11-15 illustrate still an exemplary embodiment of a surgical device 180 that includes a plurality of fluid conduits, e.g., a plurality of extendable arms. Having a plurality of extendable arms can allow the device 180 to provide fluid irrigation and/or fluid suction to a larger area. As shown in FIGS. 11 and 12, an annular sheath 182 includes first and second passageways 184a, 184b configured to respectively receive first and second extendable arms 186a, 186b. Although two passageways are shown in the sheath 182, the sheath 182 can include any number of passageways. The sheath 182 also includes a lumen 192 extending therethrough in which a surgical instrument 194 can be disposed. FIG. 11 shows the arms 186a, 186b in a first, distal position in which fluid can flow through the first and second arms 186a, 186b and respectively through proximal orifices 200a, 200b that are formed in the sheath 182 proximal to the sheath's distal end 196. FIG. 12 shows the arms 186a, 186b in a second, proximal position where distal ends 188a, 188b of the arms 186a, 186b have broken respective seals 190a, 190b and extend beyond a distal end 196 of the sheath 182. The sheath's distal end 196 can include formed therein first and second distal holes 198a, 198b, shown in FIGS. 13 and 14, through which the first and second arms 186a, 186b can respectively extend when in the second position or that fluid can directly flow through if the arms 186a, 186b are not distally advanced far enough in the second position to pass through the holes 198a, 198b. The holes 198a, 198b, and hence also the arms 186a, 186b, are equidistantly spaced around the sheath's distal circumference in this embodiment, but the holes 198a, 198b and the arms 186a, 186b can be spaced at any interval(s) in the sheath.

The first and second arms 186a, 186b can each be configured for fluid irrigation and for fluid suction, or the arms 186a, 186b can be individually dedicated such that one arm can be configured for fluid irrigation while the other can be configured for fluid suction. If the arms 186a, 186b are configured to each provide fluid irrigation and fluid suction, the arms 186a, 186b can be configured for simultaneous movement, e.g., manipulated using a single handle or other movement actuator controlling both arms 186a, 186b, or they can be configured for individual manipulation. If the arms 186a, 186b are configured to each provide fluid irrigation and fluid suction, the arms 186a, 186b can be fluidly coupled to the same fluid irrigation source and the same fluid vacuum source, or each of the arms 186a, 186b can have its own dedicated irrigation source and/or vacuum source. If the arms 186a, 186b are individually dedicated, one of the arms can be fluidly coupled to a fluid irrigation source while the other arm can be fluidly coupled to a fluid vacuum source. Individually dedicating the arms 186a, 186b can help reduce chances that fluid used for irrigation contains any undesirable, previously suctioned fluid because any previously suctioned fluid will not be in the arm used to provide fluid irrigation and thus cannot be undesirably mixed into the irrigation fluid. Individually dedicating the arms 186a, 186b can also allow for fluid to wash a desired area and be quickly aspirated with simultaneous fluid irrigation and fluid suction.

FIGS. 16-21 illustrate another exemplary embodiment of surgical device 210 including a fluid conduit, e.g., a rotatable ring or an adjustable cap 212, coupled to an annular sheath 214. The surgical device 210 is similar to the surgical devices discussed above, and similarly named elements in various embodiments discussed herein can be similarly configured. Generally, the sheath 214 has proximal and distal portions 216, 218 and has a lumen 220 extending therethrough that is configured to receive a surgical instrument, e.g., an endoscope 222, disposed therein. The sheath 214 also has at least one passageway extending therethrough that is formed within the sheath's tubular wall 226 and is configured to allow fluid to flow therethrough. First and second passageways 224a, 224b are illustrated in this embodiment, but the sheath 214 can have two or any other number of passageways. Proximal portions of each of the passageways 224a, 224b can be fluidly coupled to at least one of a fluid irrigation source and a fluid vacuum source through one or more tubes 236 coupled to the sheath 214 as discussed above such that fluid can flow proximally and/or distally through the passageways 224a, 224b.

The cap 212 can be disposed at the sheath's distal portion 218, preferably extending a distance proximally from the sheath's distal end 228, and be either fixedly removably coupled to the sheath 214. The cap's shape substantially conforms to the shape of the sheath 214, although the cap 212 can have any shape, and the cap 212 can have any size. The cap 212 can be configured to be movable between at least two positions to change locations of distal openings of the passageways 224a, 224b. When the cap 212 is in a first, proximal position, shown in FIGS. 18 and 19, the distal openings of the first and second passageways 224a, 224b include proximal orifices 226 such that fluid flowing through the first and second passageways 224a, 224b can be in fluid communication with the proximal orifices 226. Although four proximal orifices 226 are illustrated in this embodiment, the sheath 214 can include any number of proximal orifices. The proximal orifices 226 are located proximal to the sheath's distal end 228 and are preferably directed substantially toward the lumen 220, and more preferably directed substantially toward a position of a distal end 230 of the endoscope 222 disposed in the lumen 220. The cap 212 can be moved between the first, proximal position and a second, distal position, shown in FIGS. 20 and 21. In the second, distal position, the cap 212 covers the proximal orifices 226, such that the proximal orifices 226 are fluidly sealed, and allows the distal openings of the first and second passageways 224a, 224b to include at least one distal orifice 232 in the sheath 214 such that fluid flowing through the first and second passageways 224a, 224b is prevented from flowing through the proximal orifices 226 and can instead be in fluid communication with the distal orifices 232. Similarly, when the cap 212 is in the first position, the cap 212 covers the distal orifices 232 and uncovers the proximal orifices 226. Although two distal orifices 232 are illustrated in this embodiment, the sheath 214 can include any number of distal orifices. Furthermore, each distal orifice can optionally include a plurality of circumferentially spaced apart orifices. The first position is preferably the cap's default, initial position, but either the first or second positions can be the cap's default, initial position.

The cap 212 can be moved between the first and second positions in a variety of ways. The cap's movement is preferably from a location proximal to the cap 212, and more preferably from a location configured to be outside a patient's body when at least the distal portion 218 of the sheath 214 is disposed in a patient. As illustrated in this embodiment, the cap 212 can be at least partially rotatable in a clockwise direction and/or a counter-clockwise direction substantially around a central, longitudinal axis 234 of the cap 212. As will be appreciated by a person skilled in the art, in addition to or instead of being rotatable, the cap 212 can move between a plurality of positions in any one or more other ways, such as through linear movement substantially parallel to the cap's central axis 234. The cap's rotation can be manually, electrically, or otherwise effectuated as will be appreciated by a person skilled in the art. Rotating the cap 212 in one direction, e.g., clockwise, can expose the proximal orifices 226 to the passageways 224a, 224b for fluid communication between the two and can cover the distal orifices 232 to prevent fluid communication between the distal orifices 232 and the passageways 224a, 224b, while rotating the cap 212 in an opposite direction, e.g., counter-clockwise, can expose the distal orifices 232 to the passageways 224a, 224b and cover the proximal orifices 226. Preferably, rotating the cap 212 as far as possible in a particular direction fully exposes the desired orifices and fully covers the other, undesired orifices such that it can be more easily apparent when the cap 212 is in a desired position to expose a desired distal opening of the passageways 224a, 224b because the cap's rotational movement in that direction ceases. Alternatively, the cap 212 can be rotatable in one or both of the clockwise and counter-clockwise directions and have at least two locked positions within its range of rotational motion. At least one locked position can correspond to the first, distal position, and at least one locked position can correspond to the second, proximal position. One or more stop elements, e.g., a groove, a tab, corresponding protrusions and depressions, etc., formed on or in the sheath 214 can be configured for engagement with the cap 212 such that the cap 212 can "catch" the stop element(s) during its rotation to help temporarily lock the cap 212 in one of the first and second positions and such that the cap 212 can be released from the stop element(s) to move to another position. However the cap 212 is movable between positions, movement of the cap 212 to selectively expose and cover orifices in the sheath's distal portion 218 can help create a scrubbing effect adjacent one or more of the orifices because movement of a solid surface of the cap 212 over an orifice can help scrub away or unclog fluid that may have built up at the orifice during previous fluid irrigation and/or suction through the orifice.

Figure 24:
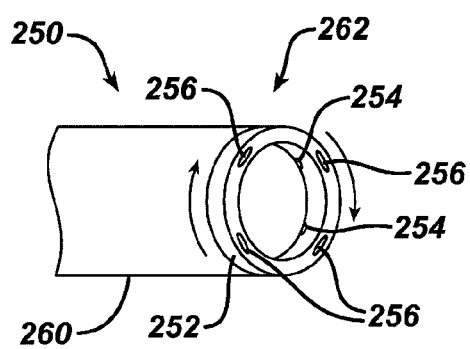
FIG. 24 is a partial perspective view of the surgical device of FIG. 22 with the ring being rotated.
Figure 25:
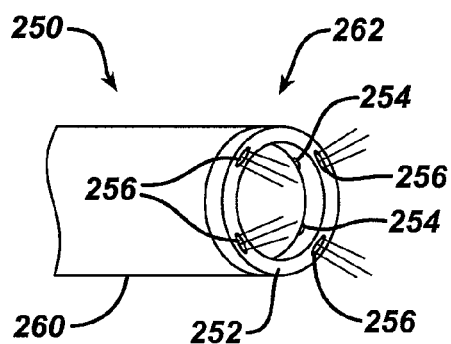
FIG. 25 is a partial perspective view of the surgical device of FIG. 24 with the ring moved into a second position.
Figure 26:
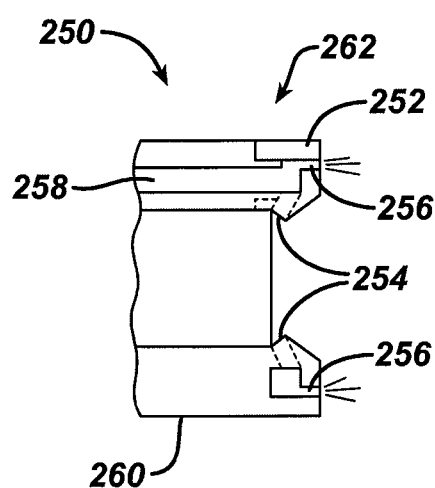
FIG. 26 is a partial cross-sectional view of the surgical device of FIG. 25.

FIGS. 22-26 illustrate another exemplary embodiment of a surgical device 250 that has a fluid conduit in the form of an adjustable cap 252 that can selectively expose and cover four proximal orifices 254 and four distal orifices 256. The cap 252 is shown in a first, proximal position in FIGS. 22 and 23 where fluid can flow through a passageway 258 having its distal opening at the proximal orifices 254. The passageway 258 in this embodiment is illustrated as a single passageway formed in the device's annular sheath 260 such that the cap 252 acts as a manifold allowing fluid to flow through a plurality of distal openings formed in the cap 252. The cap 252 can be configured to rotate, e.g., clockwise as illustrated by directional arrows in FIG. 24, to redirect fluid flow through the passageway 258 by covering the proximal orifices 254 and exposing the distal orifices 256 as shown with the cap 252 moved into a second, distal position in FIGS. 24 and 25. When the cap 252 moves between the first and second positions, the proximal orifices 254 and the distal orifices 256 can both be at least partially exposed, as illustrated in FIG. 24. In such a mid-position between the first and second positions, the cap 252 can be configured to allow fluid to flow through the passageway 258 and both distal openings 254, 256 to allow for multi-directional fluid flow at and beyond the sheath's distal portion 262. Preferably, however, the proximal and distal orifices 254, 256 and corresponding openings in the cap 252 that can expose the proximal and distal orifices 254, 256 have adequate space between them to prevent the proximal orifices 254 from being exposed when the distal orifices 256 are exposed, and vice versa.

The device disclosed herein can also be designed to be disposed of after a single use, or it can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
an annular sheath configured to be disposed in a body cavity and to receive a surgical instrument in a lumen thereof, the sheath further having a passageway configured to allow fluid to flow therethrough, and the sheath having an annular lumen in a distal portion thereof, the passageway having a plurality of proximal openings that are in fluid communication with the annular lumen and a distal opening in fluid communication with the passageway; and
a fluid conduit at least partially located in the distal portion of the sheath and configured to be movable when the sheath is disposed in a body cavity between a first position in which the fluid flowing through the passageway can exit the passageway, enter the annular lumen, and exit the annular lumen through each of the plurality of proximal openings and cannot exit through the distal opening, and a second position in which the fluid flowing through the passageway can exit the passageway through the distal opening and the fluid conduit prevents passageway of the fluid into the annular lumen such that the fluid flowing through the passageway cannot exit through the plurality of proximal openings.

2. The device of claim 1, wherein the distal opening is in a distal end of the sheath and the plurality of proximal openings are proximal to the distal end of the sheath.

3. The device of claim 1, wherein when the fluid conduit is in the first position, the fluid conduit is configured to direct fluid flowing through the passageway substantially toward the lumen, and when the fluid conduit is in the second position, the fluid conduit is configured to direct fluid flowing through the passageway away from the lumen and substantially toward a surgical field.

4. The device of claim 1, wherein the fluid conduit is configured to selectively allow for fluid irrigation through the passageway and for fluid suction through the passageway.

5. The device of claim 1, wherein the surgical instrument comprises a scope having a viewing element at a distal end of the scope.

6. The device of claim 1, wherein the fluid conduit in at least one of the first and second positions allows fluid to be directed through the passageway in a direction substantially aligned with a longitudinal axis of the passageway.

7. The device of claim 1, wherein the fluid conduit comprises an axially adjustable arm.

8. The device of claim 7, wherein the arm is configured to be movable between the first position where a distal end of the arm is proximal to a distal end of the sheath and the second position where the distal end of the arm is distal to the distal end of the sheath.

9. The device of claim 7, further comprising a self-sealing element disposed at a distal end of the sheath, wherein the arm in the first position is proximal to the self-sealing element and the arm in the second position is distal to the self-sealing element.

10. The device of claim 7, further comprising an actuator coupled to a proximal portion of the arm, wherein manipulation of the actuator is effective to move the arm between the first position and the second position.

11. The device of claim 1, wherein the fluid conduit comprises a movable ring disposed at the distal portion of the sheath.

12. The device of claim 11, wherein the ring in the first position is configured to allow fluid to flow toward the lumen of the sheath through the plurality of promixal openings and the ring in the second position is configured to allow fluid to flow away from the sheath through the distal opening, the first position being rotated from the second position.

13. The device of claim 12, wherein the ring in the first position is configured to prevent fluid flow through the distal opening of the passageway away from the distal end of the sheath and the ring in the second position is configured to prevent fluid flow through the plurality of proximal openings.

14. The device of claim 11, wherein the ring is configured to be located distal to a distal end of a surgical instrument attached to the sheath.

15. The device of claim 1, wherein when the fluid conduit is in the first position, a distal end of the fluid conduit is positioned proximal to the plurality of proximal openings and proximal to the distal opening, and when the fluid conduit is in the second position, the distal end of the fluid conduit is positioned distal to the plurality of proximal openings.

16. The device of claim 1, further comprising a seal positioned in the passageway, the fluid conduit being configured to move through the seal to break a fluid seal provided by the seal such that when the fluid conduit is in the first position, the fluid seal is not broken, and when the fluid conduit is in the second position, the fluid seal is broken.

17. The device of claim 16, wherein the seal comprises a self-sealing seal.

18. A surgical device, comprising:
- an annular sheath having first and second passageways extending therethrough, the first passageway configured to receive a surgical instrument and the second passageway configured to allow fluid to flow therethrough, the second passageway having a plurality of openings positioned proximal to a distal most opening of the second passageway, the plurality of openings being in fluid communication with one another;
- a self-sealing element disposed in the second passageway; and
- a fluid conduit configured to move between a first position in which the self-sealing element provides a fluid seal in the second passageway and a second position in which the self-sealing element does not provide a fluid seal in the second passageway, and when the fluid conduit is in the first position, fluid flowing through the second passageway can flow through each of the plurality of openings and be substantially directed toward a distal end of surgical instrument disposed in the first passageway, and when the fluid conduit is in the second position, fluid flowing through the second passageway can flow through the distal most opening of the second passageway and be substantially directed away from a distal end of the sheath and into a body cavity.

19. The device of claim 18, wherein the fluid conduit is at least partially located proximate to a distal portion of the sheath.

20. The device of claim 18, wherein the fluid conduit is configured to break the self-sealing element when the fluid conduit moves from the first position to the second position, and the self-sealing element is configured to self-seal when the fluid conduit moves from the second position to the first position.

21. The device of claim 18, wherein the second passageway includes a passageway extending longitudinally through the sheath and includes a plurality of passages angularly offset from a longitudinal axis of the sheath, the plurality of passages being positioned radially around the first passageway, and each of the plurality of passages having one of the plurality of openings at an end thereof.

* * * * *